United States Patent
Yu et al.

(10) Patent No.: US 8,981,345 B2
(45) Date of Patent: Mar. 17, 2015

(54) GRAPHENE NANORIBBON SENSOR

(71) Applicant: Electronics and Telecommunications Research Institute, Daejeon (KR)

(72) Inventors: Young-Jun Yu, Daejeon (KR); Choon Gi Choi, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 13/797,703

(22) Filed: Mar. 12, 2013

(65) Prior Publication Data

US 2014/0103296 A1   Apr. 17, 2014

(30) Foreign Application Priority Data

Oct. 17, 2012   (KR) .................. 10-2012-0115434

(51) Int. Cl.
  *H01L 29/06* (2006.01)
  *G01N 27/414* (2006.01)
  *G01N 27/12* (2006.01)
  *B82Y 15/00* (2011.01)

(52) U.S. Cl.
  CPC ............ *G01N 27/414* (2013.01); *G01N 27/127* (2013.01); *B82Y 15/00* (2013.01)
  USPC .......... 257/29; 257/40; 257/59; 257/E21.096; 438/82; 438/749; 438/748

(58) Field of Classification Search
  CPC .................................................. H01L 29/1606
  USPC .................... 257/20, 27, 29, 40, 59, 77, 253, 257/E21.096; 438/82, 749, 748
  See application file for complete search history.

(56) References Cited

U.S. PATENT DOCUMENTS

2011/0089403 A1* 4/2011 Woo et al. ........................ 257/29
2011/0227043 A1   9/2011 Guo et al.
2013/0307029 A1* 11/2013 Xu et al. ....................... 257/253

FOREIGN PATENT DOCUMENTS

KR   10-2011-0133452 A   12/2011

OTHER PUBLICATIONS

F. Schedin et al., "Detection of individual gas molecules adsorbed on graphene", Nature Materials, Sep. 2007, pp. 652-655, vol. 6, Nature Publishing Group.

* cited by examiner

*Primary Examiner* — Mark A Laurenzi

(57) ABSTRACT

Provided is a graphene nanoribbon sensor. The sensor includes a substrate, a graphene layer formed on the substrate in a first direction, and an upper dielectric layer on the graphene layer. Here, the graphene layer may have a plurality of electrode regions respectively separated in the first direction and a channel between the plurality of electrode regions.

14 Claims, 1 Drawing Sheet

GRAPHENE NANORIBBON SENSOR

CROSS-REFERENCE TO RELATED APPLICATIONS

This U.S. non-provisional patent application claims priority under 35 U.S.C. §119 of Korean Patent Application No. 10-2012-0115434, filed on Oct. 17, 2012, the entire contents of which are hereby incorporated by reference.

BACKGROUND OF THE INVENTION

The inventive concept disclosed herein relates to a sensor, and more particularly, to a graphene nanoribbon sensor.

Recently, research and development have been actively conducted on a sensor using materials having a superior conductivity such as graphene or graphene oxide (GO). Graphene is applicable to a sensor sensing molecules within a gas and bio materials by measuring surface defects and a decrease in conductivity resulted from a change of an sp2-bonded structure into an sp3-bonded structure due to the bonding between molecules to be measured. Basically, however, graphene has a high conductivity but small defects, and is thus unlikely to be used to measure molecules. Also, a graphene oxide has a low conductivity due to a number of defects.

When residues or electrical defects are present on the surface of graphene, the graphene may be adsorbed onto an external molecule. Of course, a measurement signal may also be increased by adsorbing the electric charge defects to many molecules to be measured. However, application of graphene to a sensor is now limited in a state where graphene losses its high electron transporting ability due to such defects. Therefore, development of a revolutionary structure is required for application of graphene to a sensor while graphene maintains its high electron transporting ability.

SUMMARY OF THE INVENTION

The present disclosure provides a graphene nanoribbon sensor having a high sensing sensitivity using only an edge level change of a graphene layer.

Embodiments of the inventive concept provide nanoribbon sensors including: a substrate; a graphene layer formed on the substrate in a first direction; and an upper dielectric layer on the graphene layer, wherein the graphene layer has a plurality of electrode regions respectively separated in the first direction and a channel region between the plurality of electrode regions, and the channel region has a smaller line width than the plurality of electrode regions.

In some embodiments, the graphene layer of the channel region may have an edge exposed from the upper dielectric layer.

In other embodiments, the graphene layer may include a single layer of carbon atoms.

In still other embodiments, the graphene layer of the channel region may have a line width of about 100 nm or less.

The nanoribbon sensor further including a lower dielectric layer between the substrate and the graphene layer.

In even other embodiments, the lower dielectric layer and the upper dielectric layer may include hexagonal boron nitride.

In yet other embodiments, the lower dielectric layer and the upper dielectric layer may have the same width as the graphene layer.

In further embodiments, the lower dielectric layer, the graphene layer, and the upper dielectric layer of the same line width may have a ribbon shape in the first direction.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION OF PREFERRED EMBODIMENTS

Figure 1:
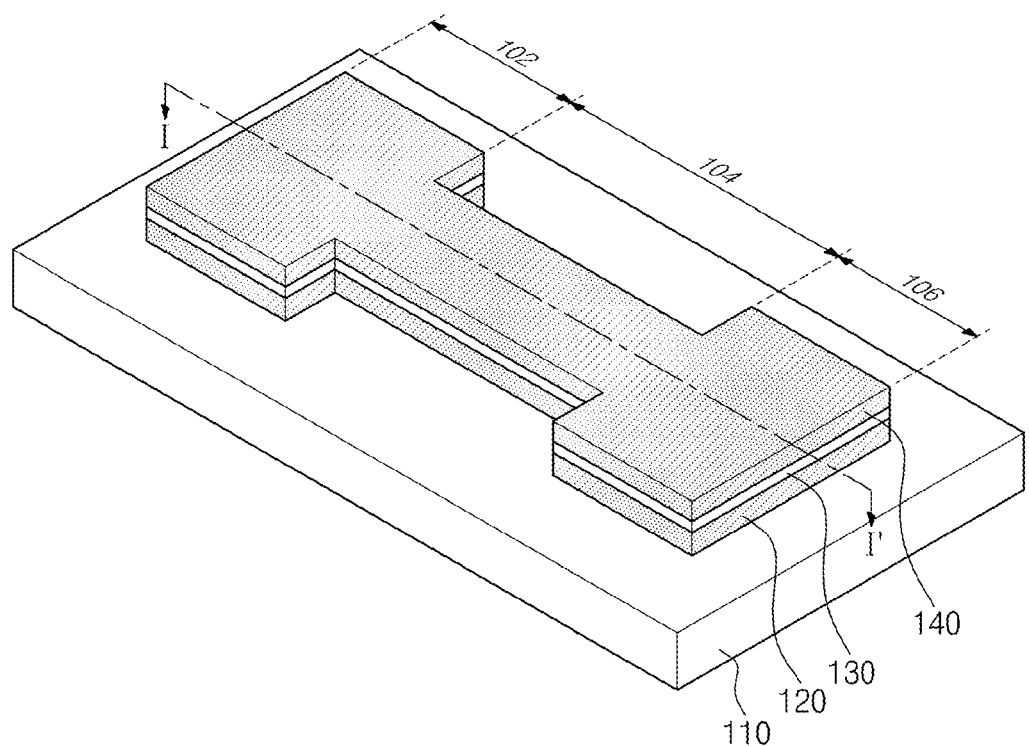
FIG. 1 is a perspective view of a graphene nanoribbon sensor according to an embodiment of the inventive concept.

Hereinafter, preferred embodiments of the inventive concept will be described in detail with reference to the accompanying drawings in such a manner that the technical idea of the inventive concept may easily be carried out by a person with ordinary skill in the art to which the invention pertains. The present disclosure may, however, be embodied in different forms and should not be construed as limited to the embodiments set forth herein.

In the drawings, anything unnecessary for describing the present disclosure will be omitted for clarity, and also like reference numerals in the drawings denote like elements.

In the specification and in all the claims, when it is described that one comprises (or includes or has) some elements, it should be understood that it may comprise (or include or has) only those elements, or it may comprise (or include or have) other elements as well as those elements if there is no specific limitation.

It will be understood that when a layer, a film, a region, or a plate is referred to as being 'on' another layer, film, region, or plate, it can be directly on the other layer, region, or plate, or intervening layers, films, regions, or plates may also be present. On the other hand, it will also be understood that when a layer, a film, an area or a plate is referred to as being "directly on" another one, intervening layers, films, areas, and plates may not be present.

Figure 2:
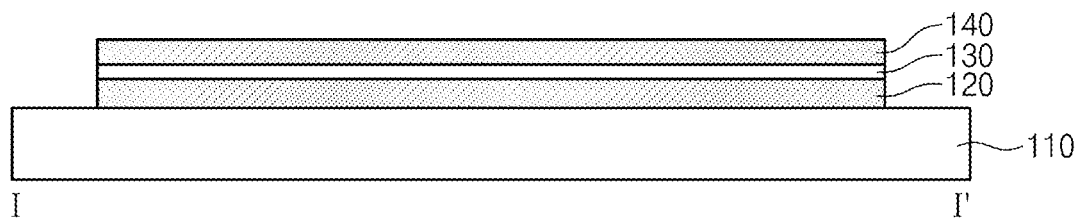
FIG. 2 is a cross-sectional view taken along line I-I' of FIG. 1.

FIG. 1 is a perspective view of a graphene nanoribbon sensor according to an embodiment. FIG. 2 is a cross-sectional view taken along line I-I' of FIG. 1.

Referring to FIGS. 1 to 2, a graphene nanoribbon sensor according to a first embodiment of the inventive concept may include a substrate 110, a lower dielectric layer 120, a graphene layer 130, and an upper dielectric layer 140.

The substrate 110 includes a metal oxide layer such as $SiO_2$, $HfO_2$, $ZrO_2$, $Ta_2O_5$ and TiO, or an insulation layer such as a silicon nitride ($Si_3N_4$) layer, on a silicon single crystal or conductor. The lower dielectric layer 120 and the upper dielectric layer 140 may include a 2-dimensional bonding material having a layered structure such as hexagonal boron nitride (h-BN).

The graphene layer 130 includes a single layer of carbon atoms bonded by the covalent bond of graphene. The graphene layer 130 may include a first electrode region 102 and a second electrode region 106 which are separated in a first direction, and a channel region 104 between the first and second electrode regions 102 and 106. The channel region 104 may have a line width smaller than the first electrode region 102 and the second electrode region 106. The channel region 104 may have the line width of 100 nm or less. Here, the first electrode region 102 and the second electrode region 106 may be a source electrode and a drain electrode in a transistor. Although not illustrated in the drawings, a gate voltage may be provided through a silicon single crystal and a conductive part which are heavily doped onto the substrate 110.

The graphene layer 130 allows a current to smoothly flow into an inside of the channel region 104. That is, electrical conductivity may be higher in the inside than an edge of the channel region 104. This is because the inside of the channel region 104 of the graphene layer 130 has a perfect 2-dimensional bonding ring through sp2 bonding. However, the edge of the channel region 104 may have a defect in a bond ring of carbon atoms. As a line width decreases, the effect of the energy level at the edge or sidewall of the graphene layer 130 on the total conductivity of the graphene layer 130 may increase. That is, an edge state influence-in the graphene channel 130 is stiffened. The graphene layer 130 may be disposed within a sandwiched structure configured by the lower dielectric layer 120 and the upper dielectric layer 140. The edge or sidewall of the graphene layer 130 is exposed to the outside from the lower dielectric layer 120 and the upper dielectric layer 140. The lower dielectric layer 120, the graphene layer 130, and the upper dielectric layer 140 are patterned at the same time by general photolithographic methods or E-beam lithographic methods.

Target molecules (not shown) to be measured may be adsorbed onto the edge or sidewall of the graphene layer 130 of the channel region 104. The adsorbed target molecules to be measured may be measured in response to a resistance change of the graphene layer 130. Since the edge state of the graphene layer 130 is changed by the adsorption of the target molecules to be measured, the resistance may be altered.

When conventional dielectrics are used, the graphene layer 130 may be directly affected by a doping change in a nanometer unit of the dielectrics in contact therewith. Thus, the electrical conductivity may be decreased due to the presence of electrical defects on the graphene surface. As described above, the lower dielectric layer 120 and the upper dielectric layer 140 include a material having a layered structure material of an atomic layer, such as hexagonal boron nitride (h-BN). The lower dielectric layer 120 and the upper dielectric layer 140 have atoms different from that of the graphene layer 130. In addition, since the lower dielectric layer 120 and the upper dielectric layer 140 have the layered structure having an atomic layer thickness which is very similar to that of graphene, the lower dielectric layer 120 and the upper dielectric layer 140 are much flatter than the conventional dielectric and have very small electrical defects. The graphene layer 130 increases the total initial conductivity of the channel by using the dielectric layer of the layered structure. Therefore, the electrical conductivity change caused by adsorbing molecules to be measured at the edge state may become more predominant.

Thus, the graphene nanoribbon sensor according to the first embodiment of the inventive concept may have a high sensing sensitivity.

The graphene nanoribbon sensor according to the embodiment of the inventive concept may include a substrate, a lower dielectric layer, a graphene layer, an upper dielectric layer. The lower dielectric layer, the graphene layer, and the upper dielectric layer may have a stacked structure such as a sandwich structure. The graphene layer may include first and second electrode regions separated in the first direction and a channel region between the first and the second electrodes.

An edge of the graphene layer in the channel region may be exposed to the outside from the lower dielectric layer and the upper dielectric layer. As the width of the graphene channel becomes smaller, the edge of the graphene having a defect of a double bond dominantly affects an electrical conductivity constituent of an entire region the graphene channel. Bonding of target molecules to be measured to the edge of the graphene layer may lead to the change in the electrical conductivity of the channel region. The edge level may increase the electrical conductivity change of the graphene layer.

Therefore, the graphene nanoribbon sensor according to the embodiments of the inventive concept can have a high sensing sensitivity.

Until now, preferred embodiments of the inventive concept are described mainly. It will be understood by those skilled in the art that various changes in form and details may be made therein without departing from the spirit and scope of the invention as defined by the appended claims. Therefore, the preferred embodiments should be considered in descriptive sense only and not for purposes of limitation. Therefore, the scope of the invention is defined not by the detailed description of the invention but by the appended claims, and all differences within the scope will be construed as being included in the inventive concept.

What is claimed is:

1. A nanoribbon sensor comprising:
   a substrate;
   a graphene layer disposed on the substrate, a length of the graphene layer extending in a first direction;
   an upper dielectric layer disposed on the graphene layer, wherein the graphene layer has a plurality of electrode regions respectively separated in the first direction and a channel region disposed between the plurality of electrode regions, the channel region having a smaller width than a width of each of the plurality of electrode regions, and
   wherein the channel region of the graphene layer includes exposed outer sidewalls and a continuous center portion, the continuous center portion having a continuous and perfect two-dimensional bonding ring of carbon atoms.

2. The nanoribbon sensor of claim 1, wherein the graphene layer comprises a single layer of carbon atoms.

3. The nanoribbon sensor of claim 1, wherein the width of the graphene layer in the channel region is a width along a second direction that is perpendicular to the first direction,
   wherein the width of the graphene layer in the channel region is greater than a thickness of the graphene layer, and
   wherein the width of the graphene layer the channel region is less than or equal to 100 nm.

4. The nanoribbon sensor of claim 1, further comprising a lower dielectric layer between the substrate and the graphene layer,
   wherein a bottom surface of the lower dielectric layer and a top surface of the substrate are positioned on the same plane and a top surface of the lower dielectric layer and a bottom surface of the graphene layer are positioned on the same plane.

5. The nanoribbon sensor of 1, wherein the lower dielectric layer and the upper dielectric layer comprise hexagonal boron nitride.

6. The nanoribbon sensor of claim 1, wherein the lower dielectric layer and the upper dielectric layer have the same width as the graphene layer.

7. The nanoribbon sensor of claim 6, wherein the lower dielectric layer, the graphene layer, and the upper dielectric layer having the same width have a ribbon shape in the first direction.

8. A sensor comprising:
a substrate;
a lower dielectric layer disposed on the substrate and extending in a first direction;
a graphene layer disposed on the lower dielectric layer and extending in the first direction, the graphene layer including first and second portions and a third portion disposed between the first and second portions, a first width of the first portion and a second width of the second portion in a second direction being greater than a third width of the third portion in the second direction, the second direction being perpendicular to the first direction; and
an upper dielectric layer disposed on the graphene layer and extending in the first direction,
wherein the third portion of the graphene layer includes exposed outer sidewalls and a continuous center portion, the continuous center portion of the third portion having a continuous and perfect two-dimensional bonding ring of carbon atoms.

9. The sensor of claim 8, wherein the first portion and the second portion of the graphene layer are a first electrode region and a second electrode region, respectively, and the third portion is a channel region of the graphene layer.

10. The sensor of claim 8, wherein the outer sidewalls of the third portion include a defect in a bonding ring of carbon atoms in the graphene layer.

11. The sensor of claim 8, wherein the third width of the third portion of the graphene layer is less than or equal to 100 nm.

12. The sensor of claim 8, wherein the lower dielectric layer and the upper dielectric layer have a layered structure with an atomic layer thickness.

13. The sensor of claim 8, wherein the lower dielectric layer, the graphene layer, and the upper dielectric layer have an I-shape in a plan view.

14. The sensor of claim 13, wherein the lower dielectric layer, the graphene layer, and the upper dielectric layer are aligned in a sequentially stacked structure, the lower dielectric layer covering substantially all of a bottom surface of the graphene layer, and the upper dielectric layer covering substantially all of a top surface of the graphene layer.

* * * * *